United States Patent
Kroll et al.

(10) Patent No.: US 7,158,826 B1
(45) Date of Patent: *Jan. 2, 2007

(54) SYSTEM AND METHOD FOR GENERATING PAIN INHIBITION PULSES USING AN IMPLANTABLE CARDIAC STIMULATION DEVICE

(75) Inventors: Mark W. Kroll, Simi Valley, CA (US); Eric Fain, Menlo Park, CA (US)

(73) Assignee: Pacesetter, Inc., Sylmar, CA (US)

( * ) Notice: Subject to any disclaimer, the term of this patent is extended or adjusted under 35 U.S.C. 154(b) by 499 days.

This patent is subject to a terminal disclaimer.

(21) Appl. No.: 10/428,217

(22) Filed: Apr. 30, 2003

(51) Int. Cl.
*A61N 1/39* (2006.01)
(52) U.S. Cl. .................. 607/5; 607/7; 607/63
(58) Field of Classification Search .......... 607/4, 607/5, 7, 9, 46, 63, 48
See application file for complete search history.

(56) References Cited

U.S. PATENT DOCUMENTS

| | | | | |
|---|---|---|---|---|
| 4,979,507 A * | 12/1990 | Heinz et al. | ............ | 607/28 |
| 5,109,847 A * | 5/1992 | Liss et al. | ............ | 607/46 |
| 5,366,484 A * | 11/1994 | Kroll | ............ | 607/5 |
| 5,464,429 A * | 11/1995 | Hedberg et al. | ............ | 607/4 |
| 5,630,834 A | 5/1997 | Bardy | ............ | 607/5 |
| 5,662,689 A | 9/1997 | Elsberry et al. | ............ | 607/5 |
| 5,722,994 A * | 3/1998 | Noren et al. | ............ | 607/5 |
| 5,792,187 A | 8/1998 | Adams | ............ | 607/5 |
| 5,817,131 A | 10/1998 | Elsberry et al. | ............ | 607/5 |
| 5,830,236 A * | 11/1998 | Mouchawar et al. | ............ | 607/5 |
| 5,906,633 A | 5/1999 | Mouchawar et al. | ............ | 607/5 |
| 5,987,354 A | 11/1999 | Cooper et al. | ............ | 607/5 |
| 6,091,989 A | 7/2000 | Swerdlow et al. | ............ | 607/5 |
| 6,349,233 B1 | 2/2002 | Adams | ............ | 607/5 |
| 6,438,418 B1 | 8/2002 | Swerdlow et al. | ............ | 607/5 |
| 6,519,493 B1 | 2/2003 | Florio et al. | ............ | 607/9 |
| 2002/0116030 A1 * | 8/2002 | Rezai | ............ | 607/9 |

FOREIGN PATENT DOCUMENTS

| WO | WO 97/09088 | 3/1997 |
|---|---|---|
| WO | WO 99/51300 | 10/1999 |

* cited by examiner

Primary Examiner—George R. Evanisko
Assistant Examiner—Michael Kahelin

(57) ABSTRACT

Improved pre-pulse pain inhibition (PPI) techniques are provided for reducing pain caused by cardioversion shocks, including a technique for determining preferred pulse durations for high voltage PPI pulses. Techniques for generating both low voltage and high voltage PPI pulses are also set forth. In one example, a train of low voltage pre-pulses is delivered to the heart, followed by a single high voltage "sliver" pulse, followed by a main high voltage cardioversion shock. The train of low voltage pre-pulses is delivered while alternating between atrial and ventricular tip electrodes, with the device housing used as a return electrode. The sliver pulse, which may be only 20 or 30 microseconds in duration, is instead delivered between electrodes implanted in the heart, such as between the RV coil and SVC coil. The main shock is delivered between the RV coil and the device housing.

18 Claims, 6 Drawing Sheets

SYSTEM AND METHOD FOR GENERATING PAIN INHIBITION PULSES USING AN IMPLANTABLE CARDIAC STIMULATION DEVICE

CROSS-REFERENCE TO RELATED APPLICATIONS

This application is related to copending U.S. patent application Ser. No. 10/428,222, titled "System and Method for Generating Pain Inhibition Pulses Using an Implantable Cardiac Stimulation Device"; and Ser. No. 10/428,237, titled "System and Method for Generating Pain Inhibition Pulses Using an Implantable Cardiac Stimulation Device", both filed concurrently herewith.

FIELD OF THE INVENTION

The invention generally relates to implantable cardiac stimulation devices such as implantable cardioverter/defibrillators (ICDs) and, in particular, to techniques for generating pain inhibition pulses prior to a main cardioversion or defibrillation shock to reduce pain associated with the main shock.

BACKGROUND OF THE INVENTION

Atrial fibrillation ("AF") is a heart arrhythmia wherein the atria of the heart beat chaotically thereby providing generally poor conduction of blood into the ventricles of the heart and hence reducing the flow of blood throughout the body. AF has been shown to lead to long-term health problems such as increased risk of thrombolytic stroke. AF can also cause reduced cardiac efficiency, irregular ventricular rhythm and unpleasant symptoms such as palpitations and shortness of breath. In some cases, AF can trigger ventricular fibrillation (VF) wherein the ventricles of the heart beat chaotically thereby providing little or no blood flow to the brain and other organs. VF, if not terminated, is usually fatal.

Hence, it is highly desirable to terminate AF. The current, most common therapy for atrial fibrillation is the administration of anti-arrhythmic drugs that control atrial and ventricular rates during atrial fibrillation. However, these drugs can actually be proarrhythmic, causing the arrhythmia to worsen. At best, anti-arrhythmic drugs appear to provide short-term therapy. Another technique for terminating AF is to administer an electrical cardioversion shock to the atria of the heart. The cardioversion shock, if successful, terminates the chaotic pulsing of the atria and causes the atria to resume a normal beating pattern. Patients prone to AF may have an ICD implanted therein capable of detecting AF and automatically administering one or more cardioversion shocks to terminate AF. Typically, about two joules of energy is administered within each cardioversion shock at an initial voltage of between 100 to 500 volts (V). The duration of the pulse is usually between 5–15 milliseconds (ms). State or the art ICDs are also capable of detecting a wide variety of other heart arrhythmias, such as VF, and for administering appropriate therapy as well. For VF, the ICD administers a much stronger cardioversion shock (referred to as a defibrillation shock) directly to the ventricles of the heart. The defibrillation shock has at least ten to twelve joules of electrical energy. Note that, herein, "cardioversion" refers to the delivery of any electrical shock intended to synchronize action potentials of myocardial cells within the heart to terminate arrhythmias. Defibrillation refers to a type cardioversion specifically intended to terminate fibrillation.

Although atrial cardioversion shocks have been found to be effective for terminating AF within many patients, the shocks can be quite painful. One reason is that the patient is typically conscious and alert at the time the shock is administered. In contrast, the much stronger ventricular defibrillation shocks for terminating VF are typically not administered until the patient has lost consciousness and hence the patient may feel only residual chest pain upon being revived. Because AF is not usually immediately life-threatening, painful cardioversion shocks for its treatment are often perceived by patients as being worse than the condition itself and therefore not tolerated. Indeed, anxiety arising from the fear of receiving a painful cardioversion shock may be sufficient to raise the heart rate sufficiently to trigger the shock. As some patients have hundreds of AF episodes per year, techniques for reducing the pain associated with cardioversion shocks are highly desirable. It is also desirable to reduce pain associated with ventricular defibrillation shocks. Although patients receiving ventricular defibrillation shocks are usually unconscious when the shock is delivered, in some cases, such shocks are erroneously delivered while the patient is conscious due to a false-positive VF detection, resulting in considerable patient pain.

One method for reducing pain arising from cardioversion shocks involves altering the stimulation waveform of the shock to, for example, reduce or smooth initial voltage peaks. See, for example, U.S. Pat. No. 5,906,633, to Mouchawar et al., entitled "System for Delivering Rounded Low Pain Therapeutic Electrical Waveforms to the Heart." Although waveform alternation techniques are promising, pain reduction typically requires a reduction in either the total shock energy or the peak shock voltage and, as such, may likewise reduce the effectiveness of the shock.

Another method for reducing pain arising from cardioversion shocks is to deliver a pre-pulse pain inhibition (PPI) pulse prior to the main shock. See, U.S. Pat. No. 6,091,989, to Swerdlow et al., entitled "Method and Apparatus for Reduction of Pain from Electric Shock Therapies." With PPI techniques, a relatively weak stimulus (the PPI pulse) is applied to the patient shortly before the main cardioversion shock. The nervous system responds to the weak stimulus in a manner such that the pain associated with the subsequent main shock is reduced or otherwise inhibited. The PPI pulse is usually either electrical or acoustic. Insofar as electrical pre-stimulus is concerned, PPI techniques have heretofore typically employed either a single relatively long, low voltage PPI pulse or a single relatively short, high voltage PPI pulse. The long, low voltage PPI pulse is usually delivered at about 12–20 volts (V). The shorter, high voltage PPI pulse is usually delivered at the voltage of the subsequent main cardioversion shock. Each has its respective advantages and disadvantages.

A significant advantage of generating a short, high voltage PPI pulse at the same voltage as the main shock is that only a single shocking capacitor is required, precharged to the main shock voltage. To instead deliver a PPI pulse at a low voltage followed by a main shock at a much higher voltage, two shocking capacitors are usually required—one precharged to the low voltage and the other precharged to the high voltage. However, high voltage PPI pulses can be painful in and of themselves. Hence, low voltage PPI pulses are typically used instead, although the extra shocking capacitor is required along with correspondingly more complicated shocking circuitry. In this regard, note that capacitors used for generating conventional pacing pulses ordinarily cannot be employed to also generate low voltage PPI pulses, which typically require a somewhat higher voltage than the pacing pulses.

In addition, both techniques share a common disadvantage, at least as conventionally implemented. The inventors have found that, for a given PPI pulse voltage, the total pulse duration is typically set to a width far greater than actually necessary to achieve adequate pain inhibition, thus consuming more energy than otherwise required and unnecessarily depleting power reserves within the implanted device. Also, insufficient consideration has been given to selecting the electrodes for use in delivering the PPI pulses, even though the choice of electrodes can affect the degree of pain inhibition achieved with a given pulse energy and voltage as well as the amount of pain caused by the PPI pulse itself.

Accordingly, it would be desirable to provide techniques for determining preferred PPI pulse durations sufficient to achieve adequate pain inhibition so that pulse energy can be minimized and energy consumption reduced. It would also be desirable to provide various PPI pulse techniques that exploit the preferred pulse durations. It would also be desirable to identify preferred electrode combinations for use in delivering PPI pulses. It is to these ends that aspects of the invention are directed.

SUMMARY

Various techniques are provided for reducing pain associated with cardioversion shocks delivered by an implantable cardiac stimulation device by using improved PPI techniques.

In accordance with a first aspect of the invention, a technique is provided for determining a preferred pulse duration for a PPI pulse delivered by an implantable cardiac stimulation device employing a shocking circuit. Initially, values for rheobase voltage and chronaxie time of nerve tissue are input. Herein, rheobase voltage refers to the minimum voltage sufficient to stimulate a nerve when using a single stimulation pulse. Chronaxie time refers to the minimum duration necessary to stimulate the nerve when using a single stimulation pulse at twice the rheobase voltage. Next, a voltage for the PPI pulse is selected and then the preferred pulse duration for that pulse voltage level is determined based upon the rheobase voltage, the chronaxie time, and the selected pulse voltage. A PPI pulse is then generated for delivering to the patient using the shocking circuit. The PPI pulse has an initial voltage set to the selected pulse voltage and has a pulse duration equal to the preferred pulse duration.

In one example, the preferred pulse duration is determined by calculating a minimum theoretical pulse duration ($d_T$) using $$d_T = \frac{V_R d_c}{V - V_R}$$

wherein V is the selected pulse voltage, $V_R$ is the rheobase voltage, and $d_C$ is the chronaxie time. For typical values of rheobase voltage and chronaxie time, the resulting minimum pulse duration is only about 27 µs at a voltage of 100 V and hence is well below the chronaxie time and is dramatically shorter than conventional PPI pulse durations, which are usually between 1–10 ms. If the shocking circuit used to deliver the PPI pulse includes a bridge circuit imposing a bridge minimum pulse duration, then the preferred pulse duration is set equal to the greater of minimum theoretical pulse duration ($d_T$) and the minimum bridge circuit pulse duration. A typical bridge minimum time is around 22 µs.

Hence, by exploiting the chronaxie time associated with nerve tissue, the duration for PPI pulses, particularly high voltage pulses, can be dramatically reduced over conventional pulse durations while still achieving adequate pain inhibition, thereby permitting a substantial reduction in pulse energy. In addition, by using extremely short pulse durations for PPI pulses, higher voltages can be employed without any substantial risk that the PPI pulses themselves will cause significant pain. Preferably, the high voltage PPI pulses are delivered between electrodes mounted within the heart, such as the right ventricular (RV) coil and the superior vena cava (SVC) coil, so that still higher voltages can be used without risk of significant pain arising from the PPI pulse itself. In particular, pain is reduced by generating the PPI pulse away from the device can or housing. Pulses instead generated using the device can as a return electrode may stimulate sensitive skin nerves and sensitive alpha motor neurons in the pectorals. The subsequent main cardioversion shock is preferably delivered using widely spaced electrodes, such as between the SVC electrode and the housing of the implanted device, to ensure maximum likelihood of success.

In accordance with a second aspect of the invention, a technique is provided for applying a high voltage PPI "sliver" pulse to a patient for use in pain inhibition. Initially, an arrhythmia of the type requiring a cardioversion shock is detected then a PPI sliver pulse is generated for delivery to the patient. The sliver pulse has a voltage set to the cardioversion shock voltage, typically 100–500 V, and has a duration substantially less than the chronaxie time of the nerve tissue intended to receive the pulse. Thereafter, a main cardioversion shock is applied at that same voltage to terminate the arrhythmia. By using the same voltage for both the PPI pulse and the main shock, complicated shocking circuitry capable of providing both a high voltage main shock and a lower voltage PPI pulse is not required. In addition, the aforementioned advantages gained by using an extremely short duration PPI sliver pulse are achieved. The sliver pulse may be either monophasic or biphasic.

In accordance with a third aspect of the invention, a train of relatively short duration, low voltage PPI pulses is generated for delivery to the patient, then a main cardioversion shock is generated for delivery at a high voltage. In one example, between ten and twenty low voltage PPI pulses are delivered over a period of no more than 60 ms, each having a pulse voltage between 7.5 and 10 volts. Exemplary individual pulse durations are 0.5 ms, with each pulse separated by 2.5 ms. By delivering a train of relatively short, low voltage PPI pulses rather than a single long low voltage pulse, pain inhibition is achieved even though the pulse voltage is below the rheobase voltage associated with most cardiac nerves (about 12 V). Moreover, by using PPI pulse voltages as low as 7.5 V, capacitors used for generating normal pacing pulses can also be used for generating the PPI pulses, thus obviating the need to provide an additional capacitor specifically for low voltage PPI. Additionally, power savings are gained when using a train of short low voltage pulses as compared to a single, long low voltage pulse. Preferably, the low voltage PPI pulses are delivered while alternating between the atrial tip electrode and the ventricular tip electrode, with the housing of the device used as a return electrode in either case. If an LV epicardial lead is implanted, the train of PPI pulses may be delivered between the LV epicardial lead and the housing of the implanted device. In one specific exemplary embodiment, both a high voltage sliver pulse and a train of low voltage PPI pulses are used for enhanced pain inhibition.

Thus, various techniques are provided for achieving improved pain reduction using PPI pulses. Other features, objects and advantages of the invention are set forth below.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
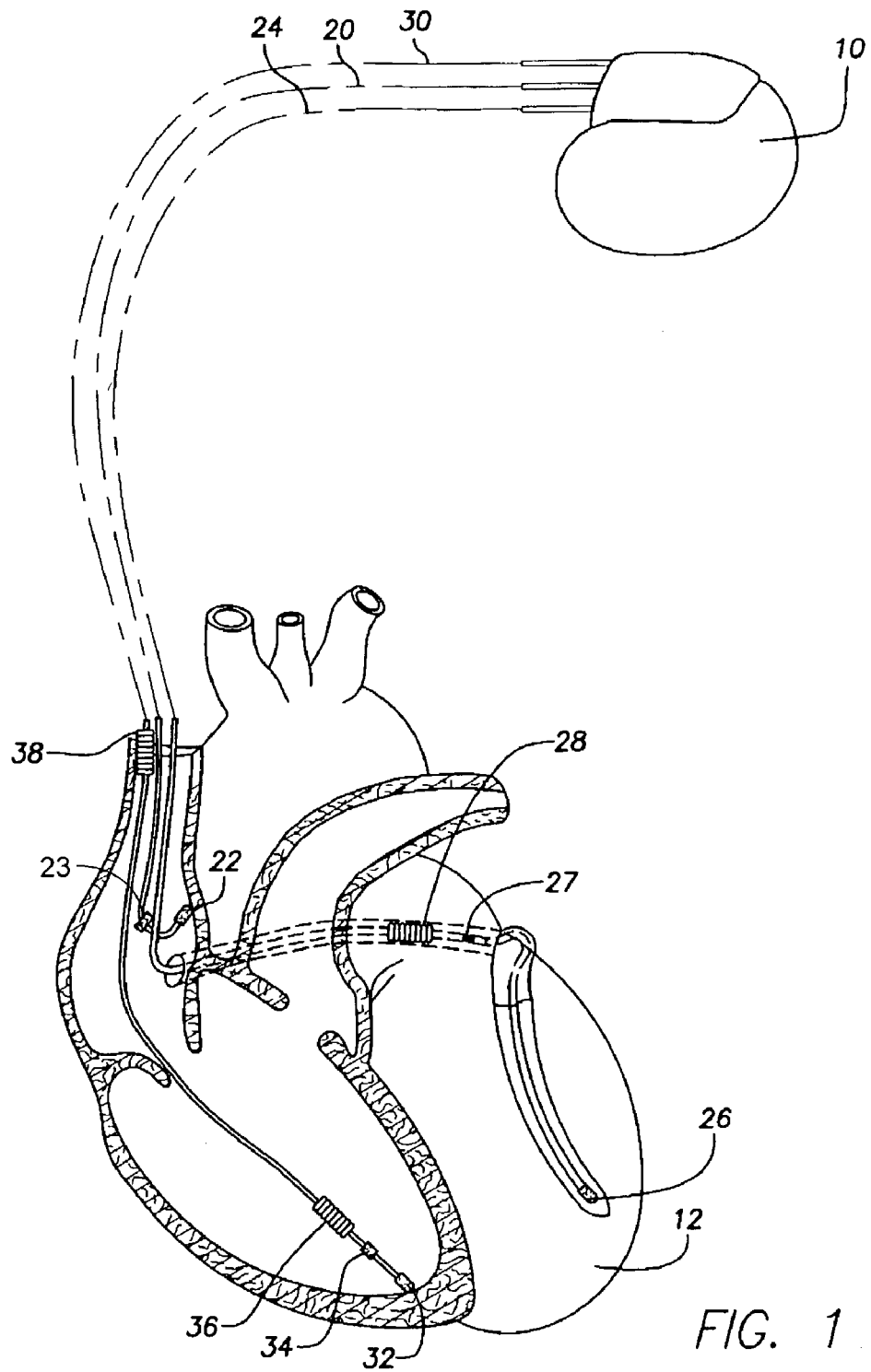
FIG. 1 is a simplified diagram illustrating an implantable stimulation device in electrical communication with at least three leads implanted into the heart of a patient for delivering multi-chamber stimulation and shock therapy including cardioversion therapy.

FIG. 1 illustrates a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular RV coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle.

Figure 2:
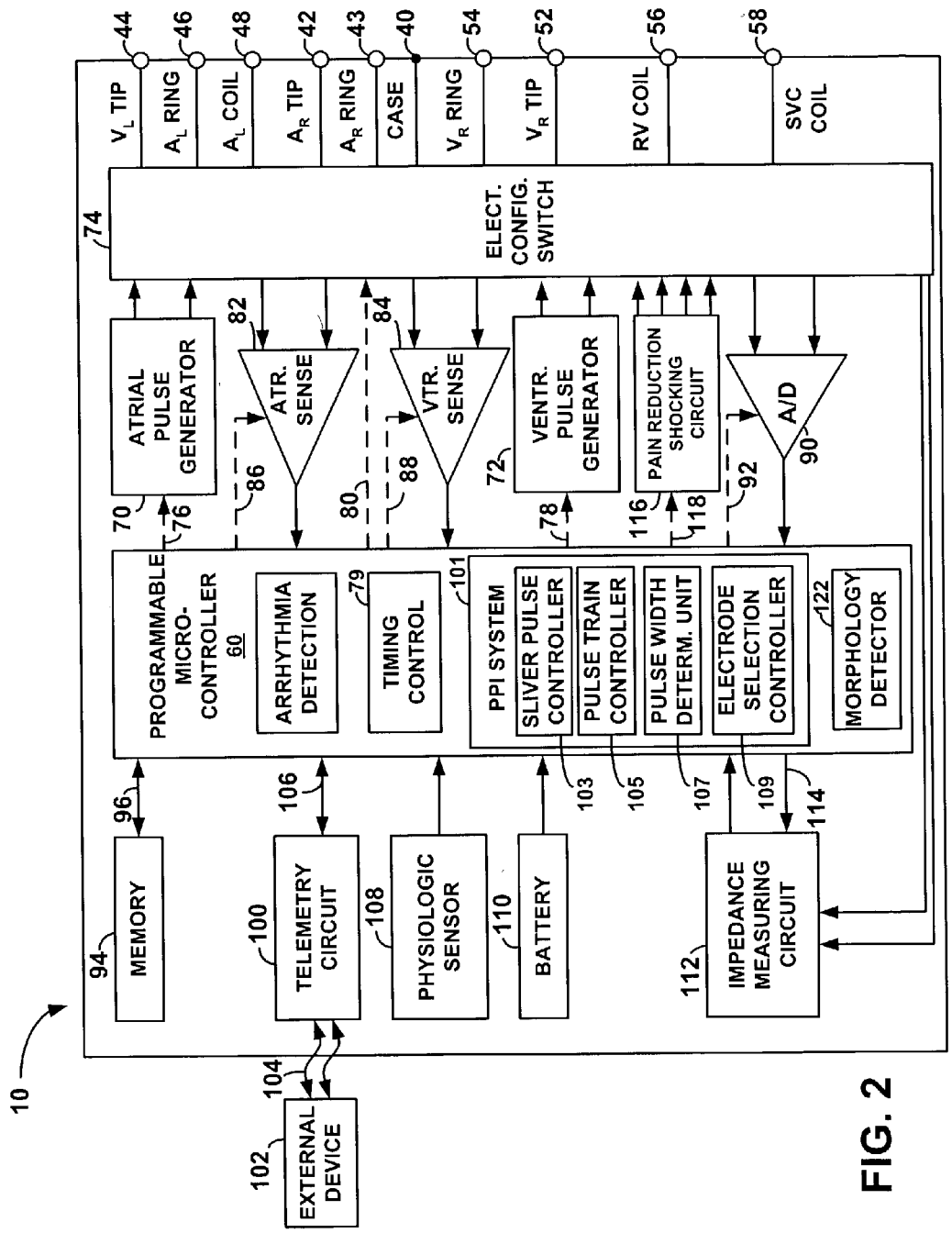
FIG. 2 is a functional block diagram of the implantable cardiac stimulation device of FIG. 1 illustrating basic elements of the stimulation device including a PPI system for controlling the delivery of PPI pulses.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22. The connector also includes a right atrial ring terminal ($A_R$ RING) 43 adapted for connection to the atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. Moreover, as theexplained in greater detail below, the microcontroller transmits signals to controlling the switch to connect a different set of electrodes for different PPI pulses and main shocking pulses to enable the PPI pulses and shocking pulses to be delivered using different sets of electrodes.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery or other power supply 110, which provides operating power to all of the circuits shown in FIG. 2. For the stimulation device 10, which employs shocking therapy, the battery 110 is capable of operating at low current drains for long periods of time, and then is capable of providing high-current pulses (for capacitor charging) when the patient requires a shock pulse. The battery 110 also has a predictable discharge characteristic so that elective replacement time can be detected. For example, the device 10 may employ lithium/silver vanadium oxide batteries. As further shown in FIG. 2, the device 10 is shown as having an impedance measuring circuit 112 which is enabled by the microcontroller 60 via a control signal 114.

To deliver cardioversion or defibrillation therapy, device 10 detects the occurrence of an arrhythmia of the type requiring such therapy, and automatically applies an appropriate electrical shock to the heart to terminate the arrhythmia. To this end, the microcontroller 60 further controls a shocking circuit 116 by way of a control signal 118. The shocking circuit 116 generates shocking pulses of low (e.g., up to 0.5 joules), moderate (e.g., 0.5–10 joules) or high energy (e.g., 11 to 40 joules), as controlled by the microcontroller 60. Such shocking pulses are applied to the heart of the patient through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). Cardioversion shocks for treatment of AF are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Shocking circuit 116 also delivers one or more PPI pulses prior to cardioversion shocks to reduce patient pain and hence is referred to herein as a pain reduction shocking circuit. The PPI pulses are generated under the control of a PPI system 101 within the microcontroller, which includes a sliver pulse controller 103, a pulse train controller 105, a pulse width determination unit 107 and an electrode selection controller 109. The sliver pulse controller controls the shocking circuit to generate an extremely short duration, high voltage PPI sliver pulse, which may be either monophasic or biphasic. The pulse train controller controls the shocking circuit to generate a train of longer duration, low voltage PPI pulses, which also may be either monophasic or biphasic. Alternatively, the low voltage PPI pulses may be generated using ventricular pulse generator 72. The pulse width determination unit determines or selects the duration of the PPI pulses based on the voltage and other factors. Depending upon the implementation, either a single sliver pulse or a train of low voltage pulses, or both, can be generated to provide maximum pain inhibition. The electrode selection controller controls switch 74 to deliver PPI pulses using particularly combinations of electrodes, chosen to achieve adequate pain inhibition while minimizing pulse energy. The operation of PPI pulse controller 101 in combination with shocking circuit 116 and switch 74 is described below. Although shown as being part of the microcontroller, the PPI system and its various components may instead be implemented as separate components. The pain reduction shocking circuit may alternatively be implemented as separate components for the main shock and for the PPI shocks.

Referring to the remaining figures, flow charts and other drawings provide an overview of the operation and novel features of stimulation device 10 as configured in accordance with exemplary embodiments of the invention. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

Improved PPI Techniques

Figure 3:
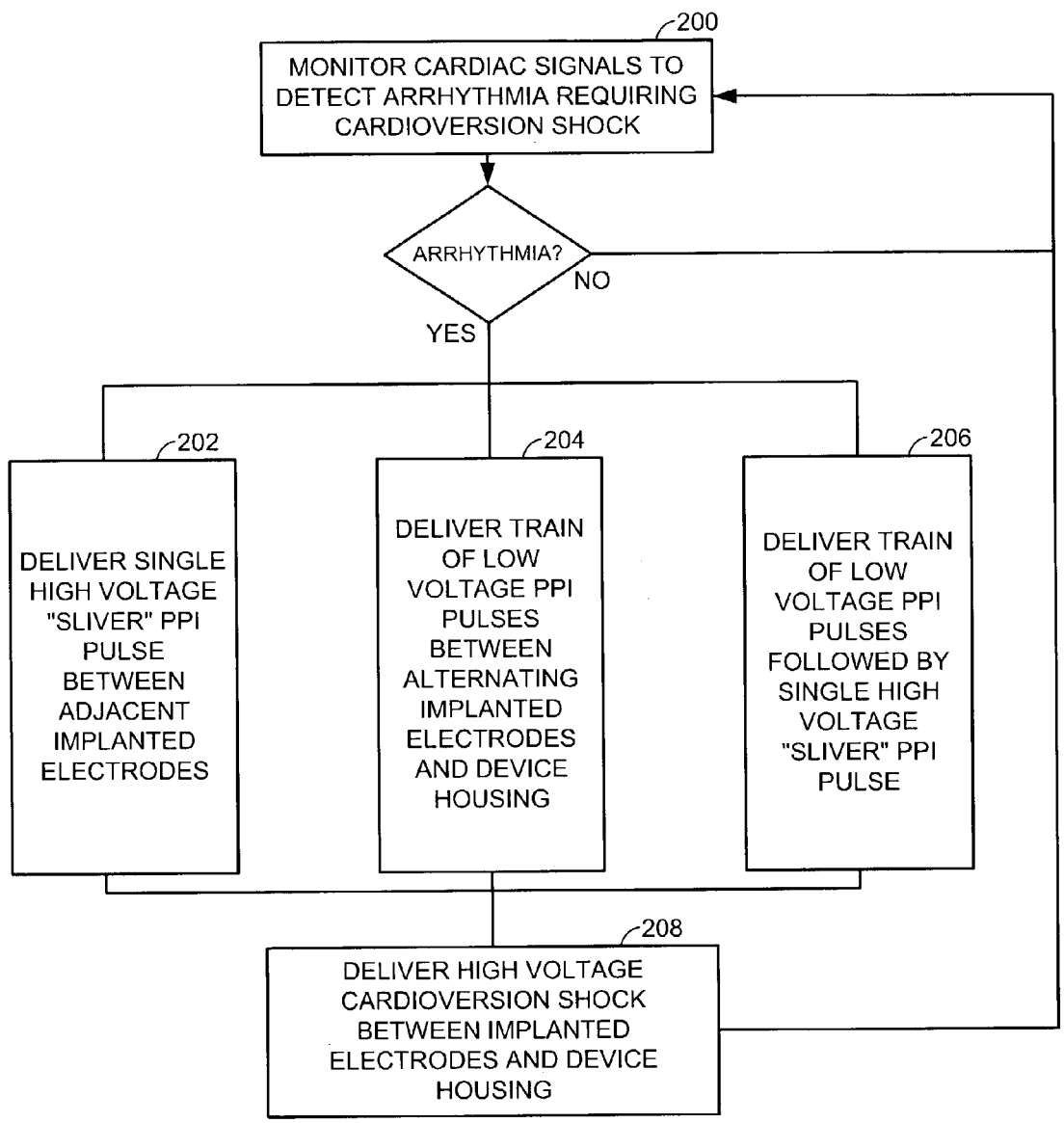
FIG. 3 is a flow chart providing an overview of exemplary techniques for generating PPI pulses prior to a cardioversion shock under the control of the PPI system of FIG. 2.

FIG. 3 illustrates operations performed by the implanted device of FIG. 2 for use in reducing pain associated with cardioversion shocks applied to terminate AF. Similar steps may be performed to reduce pain associated with defibrillation shocks applied to terminate ventricular arrhythmias. Initially, at step 200, the implanted device inputs electrical cardiac signals from the leads illustrated in FIG. 1 and processes the signals to detect the onset of an arrhythmia requiring cardioversion, such as AF or VF. In one implementation, to detect AF, the device tracks the atrial rate based on intrinsic P-waves and, if the atrial rate exceeds some AF detection threshold (AFDT), AF is presumed. In any case, if cardioversion is required, the PPI system (101 of FIG. 2), then performs one of three different PPI pain reduction procedures prior to delivery of a high-voltage cardioversion shock. Briefly, with a first pain inhibition procedure, step 202, a single high-voltage monophasic or biphasic sliver pulse is delivered between fairly closely adjacent electrodes mounted within the heart, such as between the RV coil 36 and the SVC coil 38 (FIG. 1). With a second procedure, step 204, a train of low voltage monophasic or biphasic pulses are delivered between the device housing and one or more electrodes implanted within the heart, such as between the device housing and atrial tip electrode 22 (also FIG. 1) or between the device housing and the ventricular tip electrode 26 (also FIG. 1.) Preferably, individual pulses within the train of pulses are generated while alternating between the atrial and ventricular tip electrodes. With a third procedure, step 206, a train of low voltage monophasic or biphasic pulses are delivered followed by a single high-voltage monophasic or biphasic sliver pulse. Again, preferably, the low voltage pulses are delivered between tip electrodes within the heart and the device housing whereas the high-voltage sliver pulse is delivered between fairly closely adjacent electrodes implanted within the heart. The pulses generated by steps 202–206 are graphically illustrated within FIGS. 4–7, which will be described in greater detail below.

Following the pain reduction procedure, a high-voltage cardioversion shock is delivered, at step 208, in accordance with otherwise conventional techniques. In this regard, the pain reduction shocking circuit (circuit 116 of FIG. 2) used to generate both the PPI pulses and the cardioversion shocks may be configured generally in accordance with otherwise conventional circuit techniques. For exemplary shocking circuits, see the aforementioned patent to Swerdlow et al., which is incorporated herein by reference. Pulse smoothing may also be performed to further reduce pain associated with the cardioversion shock. Techniques for smoothing cardioversion shocks are set forth in U.S. application Ser. No. 09/967,652, of Kroll et al., entitled "System And Method Of Generating A Low-Pain Multi-Step Defibrillation Waveform For Use In An Implantable Cardioverter/Defibrillator (ICD)", filed Sep. 28, 2001, which is incorporated herein by reference. The Kroll et al. patent also provides exemplary shocking circuits. Note that, since pulse smoothing is only employed as a secondary pain reduction technique, the pulses need not be smoothed as much as might otherwise be employed if smoothing were the only pain reduction technique, and so there is no significant risk of loss of effectiveness in the main shock. In any case, following delivery of the cardioversion shock, processing returns to step 200 for further monitoring of the electrical cardiac signals to determine if the arrhythmia was properly terminated. If not, the pain reduction procedure is delivered yet again before a second cardioversion shock is delivered. Although not shown in FIG. 3, for AF, if several cardioversion shocks fail to defibrillate the atria, the implantable device may suspend further delivery of cardioversion shocks to permit the patient to seek medical attention. For VF, defibrillation shocks are repeatedly applied until VF is terminated.

In addition, although not shown, during step 200, overdrive pacing techniques may be employed to help prevent the onset of AF or VF. A particularly effective overdrive pacing technique for the atria, referred to as dynamic atrial overdrive (DAO) pacing, is described in U.S. Pat. No. 6,519,493 to Florio et al. A technique for providing multiple-tiered cardioversion and DAO therapy is described in U.S. patent application Ser. No. 10/374,835, of Kroll, entitled "System and Method for Providing Cardioversion Therapy and Overdrive Pacing Using an Implantable Cardiac Stimulation Device", filed Feb. 25, 2003. The techniques described therein may be used in conjunction with the techniques of the invention.

Figure 4:
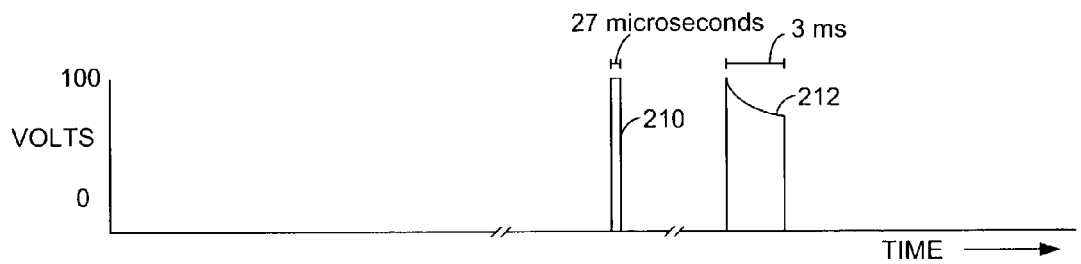
FIG. 4 is a graph illustrating a single high voltage monophasic "sliver" PPI pulse delivered prior to a cardioversion shock in accordance with the method of FIG. 3.

With reference to FIGS. 4–7, the exemplary pain inhibition procedures of steps 202–206 of FIG. 3 will now be described in greater detail. FIG. 4 illustrates a high-voltage monophasic sliver pulse 210 delivered prior to a cardioversion shock 212 in accordance with step 202. The duration of the exemplary sliver pulse is extremely short, only about 27 µs; whereas the duration of the exemplary cardioversion shock is much longer, about 3 ms. Hence, the sliver shock is over 100 times shorter than the subsequent cardioversion shock. The time delay between the sliver pulse and the cardioversion shock is about 80 ms. The delivery of the PPI pulse is timed, in accordance with otherwise conventional techniques, so as to reduce the likelihood that it might be pro-arrhythmic and in particular to avoid triggering VF (assuming VF has not already occurred). Note that the horizontal time axis of FIG. 4 is not shown to scale due to great differences in pulse duration. Instead, within FIG. 4 (as well as within FIGS. 5–7), the horizontal time axis is shown as a "broken" axis to emphasize that the duration of the pulses is not to scale and to further emphasize that the time interval between the pulses is also not to scale. Also, note that, within the figures, only a first phase of the cardioversion shock is shown. In practice, the cardioversion shock may have multiple phases, in accordance with otherwise conventional techniques.

The initial voltages for both the exemplary sliver pulse and the exemplary cardioversion shock are substantially the same, about 100 V. The voltage of the cardioversion shock decreases exponentially during the shock due to capacitor discharge. The voltage of the sliver pulse does not drop appreciably due to its extremely short duration. A significant advantage of the setting the sliver pulse and the cardioversion shock to have the same initial voltage is that separate capacitors are not required to generate the two pulses. Rather, a single capacitor is pre-charged to the shock voltage (i.e. 100 V), then discharged just long enough to generate the sliver pulse (27 µs). Given the extremely short duration of the pulse, the capacitor does not appreciably discharge. Hence, the shocking capacitor remains precharged to about 100 V to generate the main cardioversion shock 80 ms later. Any slight decrease in capacitor voltage could be compensated for by re-charging the capacitor during that 80 ms period, though that is not necessary.

Moreover, by assuring that the sliver pulse has an extremely short duration, any significant pain associated with the sliver pulse itself is substantially avoided despite its high-voltage. In addition, energy consumed by the pulse is minimal. Nevertheless, due to its high voltage, the sliver pulse significantly inhibits pain associated with the subsequent cardioversion shock. Additionally, has already noted, the sliver shock is preferably delivered between fairly closely adjacent electrodes mounted within the heart, rather than between an electrode mounted within the heart and the device housing. By delivering the high-voltage sliver pulse between two electrodes that are within the heart, pain associated with the sliver pulse itself is further reduced despite the high voltage. In particular, pain is reduced by generating the PPI pulse away from the device can. Pulses generated using the device can as a return electrode may stimulate sensitive skin nerves and sensitive alpha motor neurons in the pectorals. Then, by switching to widely spaced electrodes (such as the SVC coil and the device housing), the likelihood of properly terminating the arrhythmia is increased for the subsequent cardioversion shock because a larger "antenna" is used. The switching of the electrodes is performed by switch 74 under the control of electrode selection controller 109 (both shown in FIG. 2).

Although pulse durations of 27 μs and 3 ms are illustrated in FIG. 4 along with exemplary pulse voltages of 100 V, these values are merely exemplary. Typically, the initial voltage for both the sliver pulse and the cardioversion shock is set in the range of 100 to 500 volts. The sliver pulse duration is in the range of 10–50 μs (assuming the shocking circuit can generate a pulse that short) and the cardioversion shock duration is in the range of 1–5 ms. A technique for determining the preferred pulse duration for the sliver pulse based on pulse voltage and chronaxie nerve times is described below with reference to FIGS. 8–9.

Figure 5:
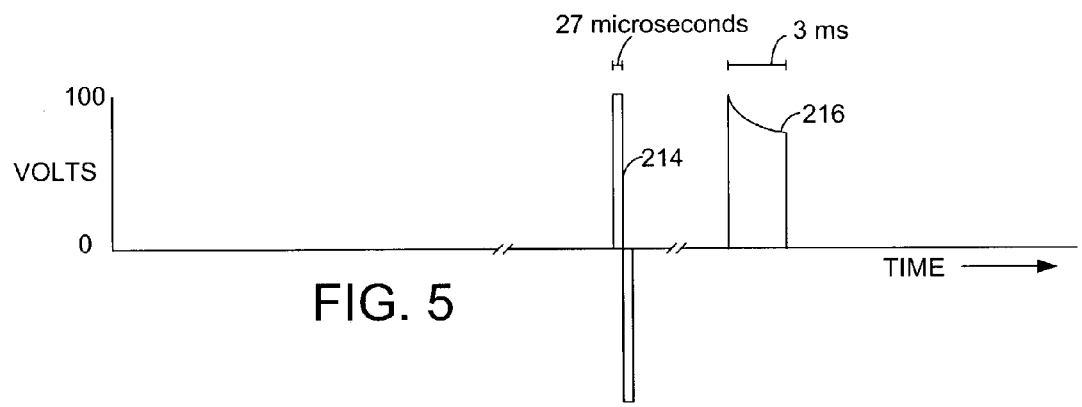
FIG. 5 is a graph illustrating a single high voltage biphasic "sliver" PPI pulse delivered prior to a cardioversion shock in accordance with the method of FIG. 3.

FIG. 5 illustrates a single high-voltage biphasic sliver pulse 214 delivered prior to a cardioversion shock 216 also accordance with step 202 of FIG. 3. As with the technique of FIG. 4, the initial voltages of the sliver pulse and the cardioversion shock are substantially the same. However, each phase of the biphasic sliver pulse is equal to the entire duration of the monophasic sliver pulse of FIG. 4. In other words, in example of FIG. 5, each phase of the biphasic sliver pulse is also 27 μs. The longer overall pulse duration is allowed, despite the same high voltage, because biphasic pulses have generally less capability to charge nerve tissue membranes. As a result, a more moderate sensation may be achieved than when using a monophasic pulse of equal voltage because the second phase cancels some of the effects of the first phase before the nerve is actually stimulated.

Figure 6:
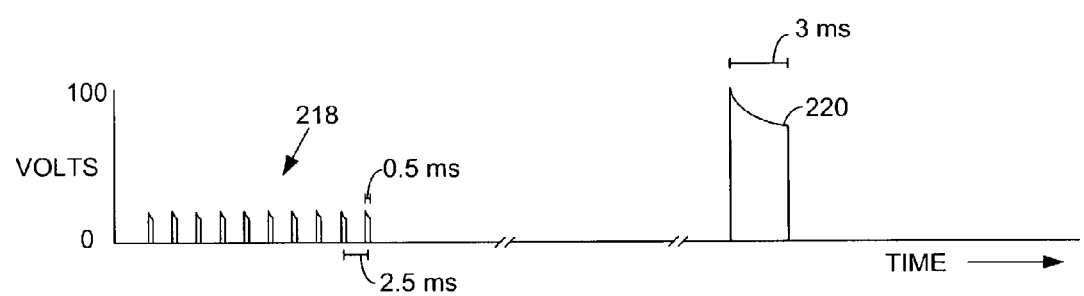
FIG. 6 is a graph illustrating a train of low voltage monophasic PPI pulses delivered prior to a cardioversion shock in accordance with the method of FIG. 3.
Figure 7:
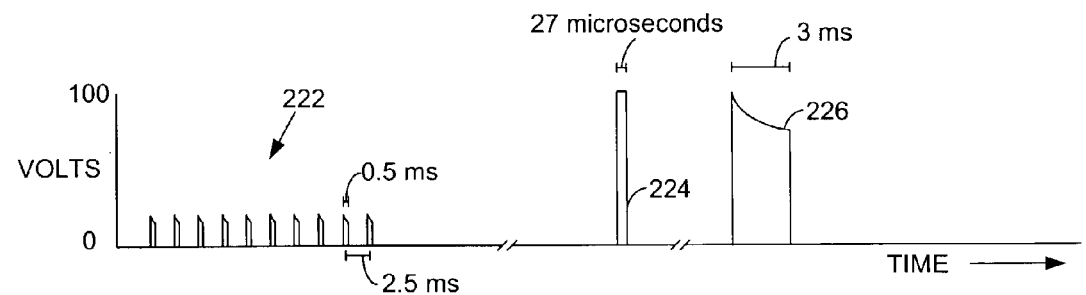
FIG. 7 is a graph illustrating a train of low voltage monophasic PPI pulses and a single high voltage monophasic PPI sliver pulse all delivered prior to a cardioversion shock in accordance with the method of FIG. 3.

With reference to FIGS. 6 and 7, the procedures of steps 204 and 206 of FIG. 3 will now be further described. Both procedures employ a train of low voltage PPI pulses delivered, either alone or in combination with a single high voltage sliver pulse. More specifically, within FIG. 6, an exemplary train of low voltage PPI pulses 218 is provided prior to a single high-voltage cardioversion shock 220. In the example, ten pulses are delivered each having a width of about 0.5 ms and having a spacing of about 2.5 milliseconds between each pulse. In other examples, 5–20 pulses are used, with voltages in the range of about 5–15 V, but preferably around 7.5V. With twenty individual pulses, the total duration of the pulse train is only about 60 ms. This permits the entire pulse train to be delivered prior to a T-wave, assuming the first pulse in the train is timed to initially depolarize the ventricles. In other words, the first pulse is timed to trigger an R-wave and then the remaining pulses are all delivered prior to the resulting T-wave, thereby helping to ensure that the PPI pulses are not pro-arrhythmic. Also, whereas the single high-voltage sliver pulse described above is preferably delivered between two electrodes implanted the heart, the low voltage pulse train is preferably delivered using at least one electrode implanted within the heart in combination with the device housing, which acts as the return electrode. The larger antenna associated with the low voltage pulses is permissible due to their low voltage.

As noted above, by delivering a train of relatively short, low voltage PPI pulses rather than a single long low voltage pulse, pain inhibition is achieved even though the pulse voltage is below the rheobase voltage associated with most cardiac nerves, which is about 12 V. Moreover, by using PPI pulse voltages as low as 7.5 V, capacitors used for generating normal pacing pulses (i.e. capacitors within ventricular pulse generator 72 of FIG. 2) can also be used for generating the PPI pulses, thus obviating the need to provide an additional capacitor within shocking circuit 116 (also FIG. 2) specifically for the low voltage PPI pulses. Additionally, power savings are gained when using a train of short low voltage pulses as compared to a single, long low voltage pulse. Preferably, the low voltage PPI pulses are generated by alternating between atrial and ventricular tip electrodes. In other words, a first pulse is delivered between the atrial tip electrode and the device housing, the second pulse is delivered between the ventricular tip electrode and the device housing, the third pulse is delivered between the atrial tip electrode and the device housing, and so on. If an LV epicardial lead is implanted, the low voltage PPI pulses are preferably delivered between the LV epicardial electrode and the device housing. This increases the chance of phrenic and pectoral nerve stimulation to further increase pain inhibition, despite the low voltage of the PPI pulses.

FIG. 7 illustrates a tiered pain reduction technique which provides a train of low voltage pulses 222, followed by a single high-voltage sliver pulse 224, followed by the high-voltage cardioversion shock 226. By providing both the train of the low voltage pulses and the high-voltage sliver shock, it is believed that pre-pulse nerve stimulation is more certain. Again, preferably, the individual pulses of the train of low voltage pulses are generated while alternating between the atrial and ventricular tip electrodes and while using the housing as the return electrode. Within FIGS. 6 and 7, the low voltage pulses are shown as monophasic pulses, however biphasic pulses may be used instead.

Thus FIGS. 4–7 illustrate the three main PPI procedures of steps 202, 204 and 206 of FIG. 3. Typically, a given implanted device is configured to implement only one of the three main procedures. However, in some implementations, the device may be configured to provide for all three procedures. If such is the case, PPI system (101 if FIG. 2) selects one of the procedures based upon programming commands previously received from an external programmer. Alternatively, the PPI system may be configured to automatically choose a particular pain reduction procedure based, e.g., on the magnitude of the cardioversion shock to be delivered. For example, if the device is configured to deliver a first cardioversion shock at a relatively low magnitude and then to increase the magnitude of cardioversion shocks if the initial shock fails to defibrillate the atria, the PPI system may be programmed to initially perform the least aggressive pain reduction procedure and to then perform more aggressive pain reduction procedures for use with more aggressive cardioversion shocks. In another example, if the implanted device is configured to allow the leads with which cardioversion shocks are delivered to be selected (either based on prior programming commands received from external programmer or based on some dynamic analysis of the electrical characteristics of the heart), then the PPI system may be programmed to choose the particular pain reduction procedure to be performed based upon the cardioversion leads that had been selected. As can be appreciated, a wider range of strategies may be employed for programming the implanted device to implement a variety of possible pain reduction protocols and no attempt will be made herein to describe all possible variations.

Pulse Width Determination Techniques

With reference to the remaining figures, techniques for determining preferred pulse durations for PPI pulses, particularly high voltage pulses, will now be described. The durations are calculated based upon chronaxie nerve time as well as other factors to ensure that the pulses have sufficient duration and pulse voltage to trigger nerve responses, thereby achieving PPI, while nevertheless consuming a minimal amount of pulse energy to thereby reduce power consumption and to reduce pain associated with the PPI pulse itself.

Figure 8:
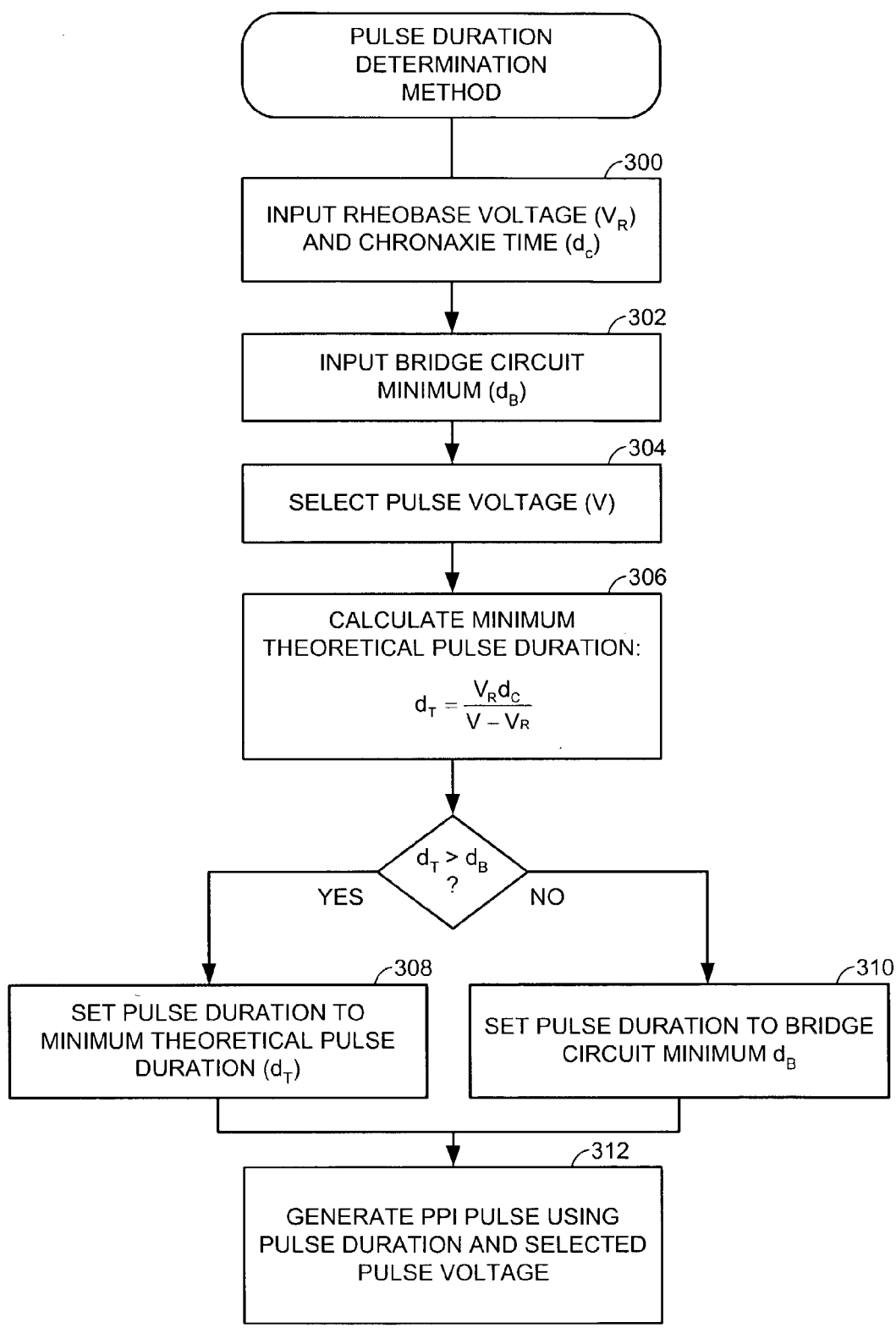
FIG. 8 is a flow chart providing an overview of an exemplary technique for determining preferred PPI pulse durations.

FIG. 8 provides an overview of an exemplary method for determining the preferred pulse width or duration for a pulse to be generated by a shocking circuit using a bridge. At step 300, a rheobase voltage $V_R$ and a chronaxie time $d_C$ are input or otherwise determined. As noted, rheobase voltage, as the term is used herein, refers to the minimum voltage that will trigger a stimulation response within a nerve using a single stimulation pulse. The chronaxie time represents the minimum interval of time necessary to electrically stimulate the nerve when using a single pulse at twice the rheobase voltage. For nerve tissue of the type that will allow for pain inhibition via PPI pulses, the rheobase voltage is typically about 12 V and the chronaxie time is typically about 200 μs. At step 302, a bridge circuit minimum time dB for the shocking circuit is input or otherwise determined. This represents the shortest duration pulse that the shocking circuit can generate. A typical bridge circuit minimum is about 22 μs. At step 304, a voltage for the PPI pulse is selected, input or otherwise determined. As noted, high voltage PPI pulse voltages for use with the invention typically range from 100–500 V.

Then, at step 306, a minimum theoretical pulse duration ($d_T$) is calculated based upon the rheobase voltage, the chronaxie time and the selected pulse voltage using:

$$d_T = \frac{V_R d_c}{V - V_R}$$

Figure 9:
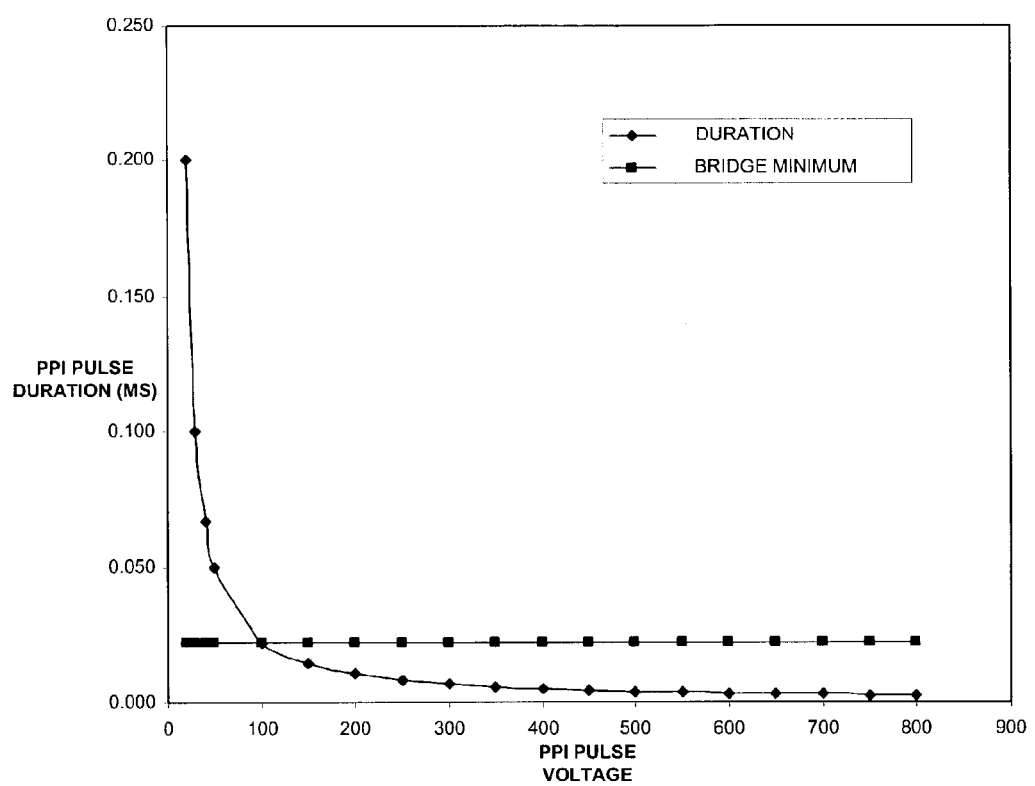
FIG. 9 is a graph illustrating the relationship of pulse duration to pulse voltage for typical PPI pulses.

For a pulse voltage of 100 V and using a rheobase voltage of 12 V and a chronaxie time of 200 μs, the theoretical minimum single pulse duration is 27 μs. Next, the calculated theoretical minimum pulse duration is compared against the bridge circuit minimum and, if it exceeds the bridge circuit minimum, the PPI pulse duration is set to the theoretical minimum pulse duration at step 308. Otherwise, it is set to the bridge circuit minimum at step 310. Finally, a PPI pulse is generated at step 312 using the calculated pulse duration and the selected pulse voltage, i.e. 27 μs at 100 V. FIG. 9 provides exemplary values for pulse duration (in milliseconds) as a function of voltage using a chronaxie time of 200 μs and a rheobase voltage of 12 V. The figure also shows a bridge minimum of 22 μs. As can be seen, for pulse voltages greater than about 100 V, the bridge minimum duration is used because it exceeds the theoretical minimum pulse duration. However, for voltages less than 100V, the theoretical pulse minimum duration may be used.

Steps 300–310 of FIG. 8 are expected to typically be performed during the design phase of a new implantable device to determine the PPI pulse duration, which is then programmed or hard-wired into the device. Alternatively, though, the device itself can be configured so as to determine the pulse duration based chronaxie times, rheobase voltages, bridge minimum and pulse voltages that are either pre-stored or are input via the telemetry circuit input system (100 of FIG. 2) from the external programmer. This is desirable if the device is configured to select from any of a wide range of pulse voltages for the PPI pulse, such as any voltage in the range of 100–500 V. If so, pulse determination unit 107 (FIG. 2) performs steps 300–310 based on chronaxie times, rheobase voltages and bridge minimum values retrieved from memory and based on a selected pulse voltage. If the pulse duration is instead specified during device design, then, typically, a pulse duration determination unit need not be incorporated within the implantable device itself.

The technique of FIG. 8 can be used to determine minimum pulse durations for any pulse voltage exceeding the selected rheobase voltage, but is particularly effective for high voltages associated with sliver pulses. As noted, the voltages of the PPI pulse trains of FIGS. 6 and 7 are below the rheobase voltage for typical cardiac nerves for a single pulse and hence the technique of FIG. 8 is not used for determining pulse durations of the low voltage pulses. It is believed that these low voltage pulses are still effective for stimulating nerves for pain inhibition, in part, because the multiple pulses of the pulse train achieve an additive effect. Also, when the low voltage PPI pulses are generated using the device can as the return electrode, the pulses help recruit nerves in the vicinity of the device, particularly sensitive skin nerves and alpha motor neurons in the pectorals, some of which may have lower rheobase voltages than cardiac nerves.

Thus, what have been described are various techniques for enhanced pain inhibition particularly for use in connection with the delivery of cardioversion shocks, including defibrillation shocks. As can be appreciated, a wide variety of techniques can be implemented consistent with the principles the invention and no attempt is made herein to describe all possible techniques. Moreover, although described primarily with reference to a combined pacer/defibrillator, the techniques of the invention may be exploited for use with non-pacing ICDs. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. A method for reducing pain associated with an electrical cardiac shock delivered to a patient by a shocking circuit of an implantable cardiac stimulation device, the method comprising:

detecting an arrhythmia requiring a cardioversion shock;

generating an electrical pre-pulse pain inhibition (PPI) sliver pulse for delivery to the patient, the sliver pulse having a voltage set to a cardioversion shock voltage level and having a duration no greater than 50 microseconds;

delivering the PPI sliver pulse to the patient via at least one electrode located in or on the patient's heart;

generating a main electrical cardioversion shock for delivery to the patient to terminate the arrhythmia, the main shock having an initial voltage also set to the cardioversion shock voltage level; and delivering the main electrical cardioversion shock to the patient.

2. The method of claim 1 wherein the voltage for both the cardioversion shock and the sliver pulse is at least 100 volts.

3. The method of claim 1 wherein the main shock has a duration of 1–3 milliseconds.

4. The method of claim 1 further comprising:

inputting a rheobase voltage and a chronaxie time associated with nerve tissue; and determining a pulse duration for the sliver pulse based upon the rheobase voltage, the chronaxie time, and the voltage of the sliver pulse.

5. The method of claim 4 wherein determining the pulse duration comprises:

calculating an minimum theoretical pulse duration ($d_T$) using $$d_T = \frac{V_R d_c}{V - V_R}$$

wherein V is the selected pulse voltage, $V_R$ is the rheobase voltage, and $d_C$ is the chronaxie time.

6. The method of claim 5 wherein the shocking circuit comprises a minimum bridge circuit time and wherein determining the pulse duration comprises setting the pulse duration equal to the greater of the minimum pulse duration ($d_T$) and the minimum bridge circuit time.

7. The method of claim 1 wherein the sliver pulse is a monophasic pulse.

8. The method of claim 1 wherein the sliver pulse is a biphasic pulse.

9. The method of claim 1 wherein the sliver pulse is delivered between a first set of electrodes and the main shock is delivered between a second set of electrodes, more widely spaced than the first.

10. The method of claim 9 wherein the sliver pulse is delivered between an RV coil and an SVC coil and wherein the main shock is delivered between the RV coil and a housing of the implantable device.

11. The method of claim 1 further comprising generating a train of non-sliver PPI pulses prior to the sliver pulse, with the train of pulses each having a voltage substantially less that that of the sliver pulse.

12. The method of claim 11 wherein each of the train of pulses has a voltage between 7.5 and 10 volts whereas the sliver pulse and the main shock have voltages of at least 100 volts.

13. The method of claim 11 wherein the train of pulses includes ten to twenty individual pulses.

14. The method of claim 11 wherein each pulse in the train of pulses has a duration of between 0.25 to 0.50 milliseconds and wherein the pulses are separated by between 2.0 and 3.0 milliseconds.

15. The method of claim 11 wherein delivery of a first pulse of the train of pulses is timed so as to depolarize the ventricles and wherein the last of the train of pulses is delivered prior to a resulting ventricular repolarization.

16. The method of claim 11 wherein the train of pulses is selectively delivered using either an atrial tip electrode or a ventricular tip electrode, with a housing of the device used as a return electrode.

17. The method of claim 16 wherein the train of pulses are delivered by alternating between the atrial tip electrode and the ventricular tip electrode.

18. A system for reducing pain associated with an electrical cardiac shock delivered to a patient by an implantable cardiac stimulation device, the system comprising:

means for generating a pre-pulse pain inhibition (PPI) sliver pulse for delivery to the patient's heart, the sliver pulse having a voltage set to a cardioversion shock voltage level and having a duration no greater than 50 microseconds; and means for generating a cardioversion shock for delivery to the patient, the main shock having an initial voltage also set to the cardioversion shock voltage level.

* * * * *